United States Patent
Agrawal et al.

(10) Patent No.: US 11,559,237 B1
(45) Date of Patent: Jan. 24, 2023

(54) ROBUST REAL-TIME EEG SUPPRESSION DETECTION DEVICE AND METHOD

(71) Applicant: NeuroWave Systems Inc., Cleveland Heights, OH (US)

(72) Inventors: Gracee Agrawal, Cleveland Heights, OH (US); Tatjana Zikov, Cleveland Heights, OH (US); Stéphane Bibian, Cleveland Heights, OH (US)

(73) Assignee: NeuroWave Systems Inc., Cleveland, OH (US)

( * ) Notice: Subject to any disclaimer, the term of this patent is extended or adjusted under 35 U.S.C. 154(b) by 669 days.

(21) Appl. No.: 16/693,802

(22) Filed: Nov. 25, 2019

Related U.S. Application Data

(63) Continuation of application No. 13/216,755, filed on Aug. 24, 2011, now abandoned.

(51) Int. Cl.
*A61B 5/316* (2021.01)
*A61B 5/00* (2006.01)
*A61B 5/369* (2021.01)

(52) U.S. Cl.
CPC .............. *A61B 5/316* (2021.01); *A61B 5/369* (2021.01); *A61B 5/7207* (2013.01); *A61B 5/742* (2013.01); *A61B 5/7405* (2013.01)

(58) Field of Classification Search
None
See application file for complete search history.

(56) References Cited

U.S. PATENT DOCUMENTS

| | | | | |
|---|---|---|---|---|
| 5,775,330 A * | 7/1998 | Kangas | ................ | A61B 5/4821 128/923 |
| 6,526,297 B1 * | 2/2003 | Merilainen | .......... | A61B 5/0059 600/472 |
| 2003/0105408 A1 * | 6/2003 | Gotman | ................ | A61B 5/316 600/544 |

(Continued)

OTHER PUBLICATIONS

Lukatch et al., Anesthetic-induced Burst Suppression EEG Activity Requires Glutamate-mediated Excitatory Synaptic Transmission, 2005, Cerebral Cortex, , 15(9), 1322-1331 (Year: 2005).*

(Continued)

*Primary Examiner* — Michael R Bloch
(74) *Attorney, Agent, or Firm* — Brian Kolkowski

(57) ABSTRACT

The present invention relates to a physiological monitor and system, more particularly to an electroencephalogram (EEG) monitor and system, and a method of detecting the presence or occurrence of suppression in the EEG signal. Accurately detecting signal suppression in real-time provides the clinician with the ability to prevent possibly severe, long-term damage to patients as a result of excessive anesthetic or sedative. The present invention provides such a system and method for accurately and automatically detecting suppression in physiological, particularly EEG, signals in real-time and allowing for the administration of treatment or medication to reverse the effects of such situations, or minimize the harm caused. The present invention also allows for the use of closed-loop treatment or drug delivery systems to further automate the process and provide rapid treatment to a patient to reverse or minimize potential harm.

20 Claims, 5 Drawing Sheets

(56) References Cited

U.S. PATENT DOCUMENTS

| | | | | |
|---|---|---|---|---|
| 2005/0137494 | A1* | 6/2005 | Viertio-Oja | A61B 5/7203 600/544 |
| 2008/0249431 | A1* | 10/2008 | Bier | A61B 5/369 604/503 |
| 2008/0317672 | A1* | 12/2008 | Viertio-Oja | G16H 40/63 424/9.1 |
| 2009/0264957 | A1* | 10/2009 | Giftakis | A61N 1/36082 607/45 |
| 2011/0218454 | A1* | 9/2011 | Low | A61B 5/369 600/544 |
| 2011/0295096 | A1* | 12/2011 | Bibian | A61B 5/291 600/372 |
| 2011/0295142 | A1* | 12/2011 | Chakravarthy | A61B 5/7203 600/544 |

OTHER PUBLICATIONS

Sleigh et al., Comparison of changes in electroencephalographic measures during induction of general anaesthesia: influence of the gamma frequency band and electromyogram signal, 2001, British Journal of Anaesthesia 86(1): 50-58 (Year: 2001).*

Rampil, Elements of EEG signal processing, 1987, International Journal of Clinical Monitoring and Computing 4: 85-98 (Year: 1987).*

* cited by examiner

ROBUST REAL-TIME EEG SUPPRESSION DETECTION DEVICE AND METHOD

CROSS-REFERENCE TO RELATED APPLICATIONS

This application is a continuation of U.S. patent application Ser. No. 13/216,755 which was filed on Aug. 24, 2011.

BACKGROUND OF THE INVENTION

1. Field of the Invention

The present invention relates to the processing of signals, and particularly to the processing of electrophysiological signals. More particularly, the present invention relates to the processing of electroencephalographic signals. More particularly still, the present invention relates to the detection and identification of suppression periods in electroencephalographic signals. Further, the present invention relates to an automated method for identification and detection of suppression periods in electroencephalographic signals.

2. Technology Review

Electroencephalography (EEG) is the recording of electrical activity from the scalp surface, which is produced by the firing of neurons in the brain. In particular, the EEG is generated by cortical nerve cell inhibitory and excitatory postsynaptic potentials. These potentials summate in the underlying cortex and extend to the scalp surface, where they are recorded as the EEG signals.

During deep anesthesia, the EEG may develop a peculiar pattern of activity known as suppression-burst pattern. This is a particular type of pseudo-periodic pattern, consisting of bursts of high-voltage activity (mixture of sharp and slow waves) periodically interrupted by episodes of suppression (low-voltage activity <10 µV). The underlying physiological changes that accompany the suppression-burst pattern during general anesthesia consist of cortical neuronal inactivity during suppression, cortical depolarization during burst, and cortical hyperpolarization just prior to the onset of suppression.

Suppression-burst pattern may be induced intentionally to reduce cerebral metabolic demand and provide possible brain protection, by administering large doses of general anesthetics. Titration to a specific degree of suppression-burst has been recommended as a surrogate end-point for barbiturate coma therapy. In addition, hypothermia has been observed to emphasize the suppression effect of general anesthesia. When not associated with a high dose of anesthetic drugs or CNS depressant drugs or hypothermia, the presence of suppression-burst pattern in EEG carries a grave prognosis due to its relation to severe encephalopathy. Some of the underlying neuropathological conditions which produce a suppression-burst pattern in EEG are head trauma, stroke, coma or anoxia.

Typically, the episodes of suppression are longer (typically 5-10 seconds) than the bursts of activity (typically 1-3 seconds). As the anesthetic depth increases and/or the patient's condition worsens, bursts become shorter, simpler and of lower amplitude; and periods of suppression become longer until complete EEG suppression (activity <10 µV) or electrocerebral silence (activity <2 µV) supervenes.

Due to the high clinical importance of the presence of suppression in EEG signals, its timely and robust detection is very important. In particular, it is extremely important to be able to accurately detect the periods of EEG suppression in real-time during general anesthesia to avoid very deep anesthetic levels. The suppression periods in EEG waveform can be manually detected by human EEG experts based on visual observation. A trained individual would either view a printout of the EEG signal or view the EEG signal on a monitor in real time. The signal would then be visually inspected for periods of time, typically longer than 0.5 s, where the peak-to-peak amplitude of the EEG signal is much less (typically 5 to 20 µV). However, this method is not very robust due to the subjectivity in the visual analysis. In addition, it is very time-consuming, tedious and expensive (due to the expertise required). Hence it is very important to develop an accurate and automated method for real-time EEG suppression detection. Therefore, the objective of the present invention is to provide an automated method for robust detection of suppression periods in EEG signals in real time.

Current automated methodologies for the detection of suppression in EEG waveform are typically carried out based on the peak-to-peak method inherited from visual observation, as described above. However, this method is particularly sensitive to noise and can fail to detect suppression in certain conditions due to the susceptibility of the EEG signal, and thus the measured peak-to-peak amplitude of the said signal, to various kinds of artifacts. EEG signals can be corrupted by various physiological artifacts such as ocular artifacts (eye blinks, rapid eye movements, etc.), muscle artifacts (head movement, biting, swallowing, facial movements, etc.) or ECG artifacts, as well as non-physiological artifacts such as electrode/lead movement, percussion from an intravenous drip, etc. These artifacts can falsely increase the measured amplitude of the EEG signal and hence can affect the ability of automated peak-to-peak measurement methods to accurately detect suppression in EEG signals.

It is therefore an objective of the present invention to provide a device, system, and method that addresses all of these needs and others where such a device, system, and method would be applicable. It is another object of the present invention that this device and method detect EEG suppression in real-time.

SUMMARY OF THE INVENTION

The present invention relates to the processing of signals, and particularly to the processing of electrophysiological signals. More particularly, the present invention relates to the processing of electroencephalographic signals. More particularly still, the present invention relates to the detection and identification of suppression periods in electroencephalographic signals. Further, the present invention relates to an automated method for identification and detection of suppression periods in electroencephalographic signals.

The accurate and real-time detection of the presence of suppression in an EEG signal allows for increased reliability in the monitoring of cortical activity, level of consciousness, level of sedation, titration for seizure treatment, presence of brain dysfunction, and the like. The suppression detection methods of the present invention, and the systems and devices using these methods can be used for anesthesia monitoring, sedation monitoring, brain dysfunction monitoring, seizure treatment titration, and the like. These methods and the systems and devices using these methods can be used with equipment for the operating room, acute care such as the intensive care unit, critical care such as the emergency room, or in the field. These methods and the systems and devices using these methods can be used by anesthesiologists, nurse anesthetists, neurologists and neurosurgeons, pulmonologists, emergency room physicians and clinicians, intensive care physicians and clinicians, medics, paramedics, emergency medical technicians, respiratory technicians, and the like. Preferably, these methods and the systems and devices using these methods can be used by individuals or clinicians with little or no training in signal analysis or processing. These methods preferably are used with anesthesia monitors, sedation monitors, seizure detectors, sleep diagnostic monitors, any sort of EEG monitor, battlefield monitors, operating room monitor, ICU monitor, emergency room monitor, and the like.

Various embodiments of the system of the present invention were developed for monitoring and processing various physiological signals from a subject. Preferably, this system is used for the monitoring of brain wave or activity from a single patient or multiple patients. Preferably, the system is a multi-channel EEG system; however, depending on purpose of use and cost, systems may have as few as 1 channel. Preferably, the system also includes one or more methods or algorithms for monitoring cortical activity, level of consciousness, level of sedation, amount of suppression, titration for seizure treatment, presence of brain dysfunction, and the like. Preferably, the system or monitor can also measure muscle activity, EMG. In addition, the system and related methods can use other sensors that measure physiological signals which directly or indirectly result in or from brain dysfunction, or effect or result from brain activity.

Preferably, the system or monitor is constructed to be rugged, so as to withstand transport, handling and use in all of the applications listed above including in emergency scenarios, such as on the battlefield or in mass casualty situations, or to reliably survive daily use by emergency medical personnel or other first responders. The system or monitor should preferably be splash-proof (or water tight), dust-tight, scratch-resistant, and resistant to mechanical shock and vibration. The system or monitor should preferably be portable and field-deployable in particular embodiments to a military theater of operation, the scene of an accident, the home of a patient, or to any clinical setting.

The system described in this invention also preferably incorporates a number of unique features that improve safety, performance, durability, and reliability. The system should be cardiac defibrillator proof, meaning that its electrical components are capable of withstanding the surge of electrical current associated with the application of a cardiac defibrillator shock to a patient being monitored by the system, and that the system remains operable after sustaining such a surge. The system should have shielded leads so as to reduce as much as possible the effects of external electromagnetic interference on the collection of biopotential or physiological signals from the patient being monitored by the system. The system should be auto-calibrating, and more preferably capable of compensating for the potential differences in the gains of the input channels to the patient module. The system should be capable of performing a continuous impedance check on its electrode leads to ensure the suitability of monitored signals.

Optionally, the system or monitor may be calibrated or tested via the utilization of a "virtual patient" device, which outputs pre-recorded digital EEG in analog format and in real time in a manner similar to what would be acquired from an actual patient, possibly with data from patients with known brain dysfunction or brain wave abnormalities, particularly EEG suppression as a result of neuropathological event or condition. This virtual patient can also output any arbitrary waveforms at amplitudes similar to those of EEG signals. These waveforms may be used for further testing of the amplification system, such as for the determination of the amplifier bandwidth, noise profile, linearity, common mode rejection ratio, or other input requirements.

The system or monitor should preferably be designed for non-expert use. By this, it is meant that a person should not be required to possess extraordinary or special medical training in order to use the system effectively and reliably. The system should therefore preferably be automatic in operation in a number of respects. First, the system should be capable of automatic calibration. Second, the system should preferably have automatic detection of input signal quality; for example, the system should be capable of detecting an imbalance in electrode impedance. Third, the system should preferably be capable of artifact detection and removal on one or more levels, so as to isolate for analysis that part of the signal which conveys meaningful information related to a subject's cortical activity, level of consciousness, level of sedation, amount of suppression, titration for seizure treatment, presence of brain dysfunction, and the like. Fourth, the system should preferably include outputs which result in visual and/or audible feedback capable of informing the user about the state of the patient related to monitoring of cortical activity, level of consciousness, level of sedation, amount of suppression, titration for seizure treatment, presence of brain dysfunction, and the like at any time during the period of time that the system is monitoring the patient.

Preferably, the system should operate in real time. One example of real-time operation is the ability of the system to monitor the cortical activity, level of consciousness, level of sedation, amount of suppression, titration for seizure treatment or presence of brain dysfunction as it is happening, rather than being limited to analysis that takes place minutes or hours afterward.

The processor or computer, and the methods of the present invention preferably contain software or embedded algorithms or steps that automatically identify artifacts and even more preferably remove the artifacts from the physiological signal, and automatically monitor cortical activity, level of consciousness, level of sedation, amount of suppression, titration for seizure treatment, presence of brain dysfunction, and the like based on the essentially artifact-free EEG signal.

One embodiment of the present invention involves method of monitoring a subject or patient under anesthesia comprising steps of: acquiring an EEG signal from a subject or patient; computing with a processor substantially at the same time as the signal is acquired the first derivative of the EEG signal; analyzing the first derivative of the EEG signal to compute at least one suppression detection parameter, the at least one suppression detection parameter being used to detect suppression periods in the EEG signal; and outputting a parameter based at least in part on the suppression detection parameter to a device for communicating the outputted parameter to a clinician monitoring the patient under anesthesia.

Another embodiment of the present invention involves method of monitoring a subject or patient under anesthesia comprising steps of: acquiring an EEG signal from a subject or patient; computing with a processor substantially at the same time as the signal is acquired the first derivative of the EEG signal; analyzing the first derivative of the EEG signal to compute at least one suppression detection parameter, the at least one suppression detection parameter being used to detect suppression periods in the EEG signal; and outputting a parameter based at least in part on the suppression detection parameter to a device for automatically controlling the patient's level of anesthesia.

Still another embodiment of the present invention involves a method of quantifying the amount of EEG suppression in a subject or patient comprising steps of: acquiring an EEG signal from a subject or patient; computing with a processor substantially at the same time as the signal is acquired the first derivative of the EEG signal; analyzing the first derivative of the EEG signal to compute at least one suppression detection parameter, the at least one suppression detection parameter being used to detect suppression periods in the EEG signal; and outputting a parameter quantifying the amount of suppression in the EEG during the last minute to a device for communicating the outputted parameter to a clinician monitoring the patient.

Still another embodiment of the present invention involves a method of quantifying the amount of EEG suppression in a subject or patient comprising steps of: acquiring an EEG signal from a subject or patient; computing with a processor substantially at the same time as the signal is acquired the first derivative of the EEG signal; analyzing the first derivative of the EEG signal and calculating the median absolute value of the first derivative of the EEG signal; comparing the median amplitude value of the first derivative of the EEG signal over a pre-determined time frame of the signal against a threshold value to identify periods of suppression; comparing the calculated suppression period length against a pre-determined time threshold; and determining if the EEG signal is presently suppressed.

Still yet another embodiment of the present invention involves a method of quantifying the amount of EEG suppression in a subject or patient comprising steps of: acquiring an EEG signal from a subject or patient; computing with a processor substantially at the same time as the signal is acquired the first derivative of the EEG signal; analyzing the first derivative of the EEG signal and calculating at least two suppression detection parameters, at least one suppression detection parameter being the median absolute value of the first derivative of the EEG signal; comparing the suppression detection parameters against a predetermined threshold value for each suppression detection parameter to identify periods of suppression; comparing the calculated suppression period length against a pre-determined time threshold; and determining if the EEG signal is presently suppressed.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DETAILED DESCRIPTION

Figure 1A:
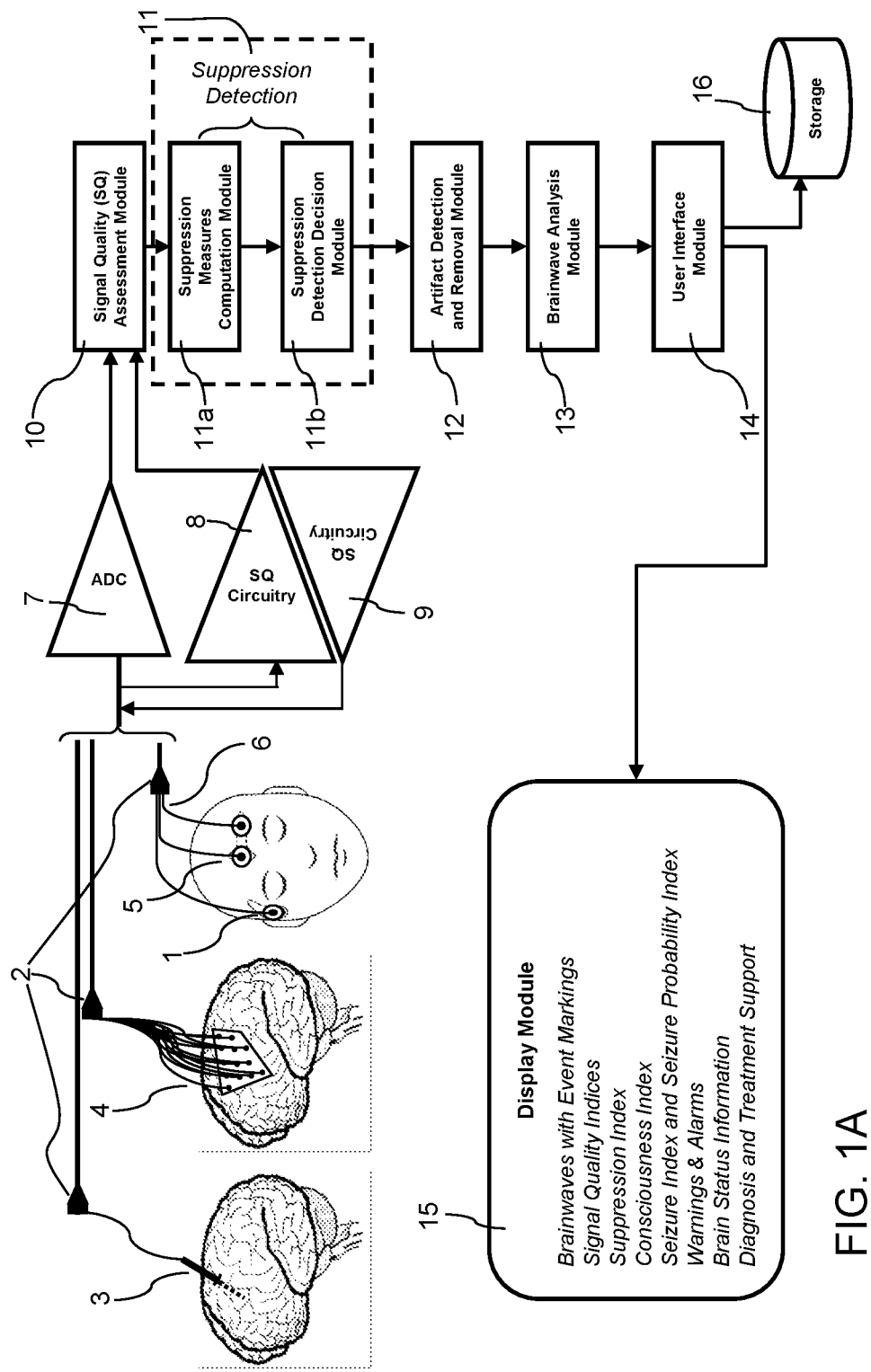
FIG. 1A. Block diagram of a system overview for real-time applications of the invention wherein various signals, parameters, measurements, and messages are displayed for a clinician to see and determine the proper course of treatment.

The present invention relates to the processing of signals, and particularly to the processing of electrophysiological signals. More particularly, the present invention relates to the processing of electroencephalographic signals. More particularly still, the present invention relates to the detection and identification of suppression periods in electroencephalographic signals. Further, the present invention relates to an automated method for identification and detection of suppression periods in electroencephalographic signals.

All embodiments of the present invention involve acquiring an EEG, other physiological signal or other sensor signal from a subject or a patient, the subject being any type of animal, including human subjects. The precise method for acquiring a signal from the subject or patient varies according to the physiological signal being acquired and analyzed. In one preferred embodiment, that is acquiring EEG signals, electrodes can be placed at various locations on the subject's scalp in order to detect EEG or brain wave signals. Common locations for the electrodes include frontal (F), temporal (T), parietal (P), anterior (A), central (C) and occipital (O). Preferably for the present invention, at least one electrode is placed in the frontal position. Additionally, preferably at least two electrodes are used—one signal electrode and one reference electrode; and if further EEG or brain wave signal channels are desired, the number of electrodes required will depend on whether separate reference electrodes or a single reference electrode is used. For various embodiments of the present invention, preferably an electrode is used and the placement of at least one of the electrodes is at or near the frontal lobe of the subject's scalp. In order to obtain a good EEG or brain wave signal, it is desirable to have low impedances for the electrodes. Typical EEG electrode connections may have impedance in the range of 5 to 10 K ohms. It is in generally desirable to reduce such impedance levels to below 2 K ohms. Therefore a conductive paste or gel may be applied to the electrode to create a connection with impedance below 2 K ohms. Alternatively or in conjunction with the conductive gel, the subject's skin may be mechanically abraded, the electrode may be amplified or a dry electrode may be used. Dry physiological recording electrodes of the type described in U.S. Pat. No. 7,032,301 are herein incorporated by reference. Dry electrodes provide the advantage that there is no gel to dry out or irritate the skin, which guaranties long shelf life and longer periods of monitoring the subject, no abrading or cleaning of the skin, and that the electrode can be applied in hairy areas such as the scalp.

Other similar methods of acquiring physiological signals may be used in the present invention which are known to those skilled in the art for acquiring signals such as electrocardiography (ECG), electrical impedance tomography (EIT), electromyography (EMG) and electro-oculography (EOG).

In some embodiments, an EEG signal is measured from a subject or patient who may be having a seizure(s). Similar to above, the patient is attached to an EEG/seizure monitoring system via some form of electrodes and electrode leads. Particularly if the patient is known to be in danger of having a seizure, the EEG signal can be analyzed watching for waveforms that are indicative of the patient having a seizure so proper medical care can be given. When a seizure is detected, the system can be used to administer drugs or medication to the subject or patient to maintain a specific level of suppression for therapeutic purposes in treating the seizure.

Other sensor signals measuring physical conditions of the subject include blood pressure measurements, galvanic skin response, respiratory effort, respiratory flow, body movement, pulse oximetry, and the like.

Another step in various embodiments involves computing with a processor, substantially at the same time as the signal is acquired, the first derivative of the physiological or sensor signal. Most embodiments utilize the first derivative, though some embodiments may use a higher derivative. Utilizing the first derivative rather than the raw (or filtered) EEG signals has been shown to remove baseline wandering and thus renders the analysis more accurate and reliable. In addition, the surface EEG signals are the time-varying signals that reflect the fluctuations in the number of activated neurons or the alternating component of the mean soma potential over time. The first derivative of EEG signal has been shown to be strongly linked to the mean soma potential based on Cellular Automaton (CA) simulations of cortical function. The step of computing the first or second derivative of the signal is performed on a processor, in real time, and substantially at the same time as the signal is being acquired. Substantially at the same time means that immediately as the signal is acquired by the circuitry and apparatus described above, the processor computes the appropriate derivative of that signal.

In various embodiments of the present invention, the acquired EEG signal may or may not be filtered prior to computing the first (or higher) derivative and analyzing the signal. In those embodiments which require signal filtering, such filtering is performed by means of a low-pass filter used to remove high frequency (HF) interference from the EEG signal. Examples of HF interference that may need to be filtered out of the EEG signal include other physiological signals such as electromyographic (EMG) signals, as well as outside HF interference such as background electrical noise and noise from electro-surgical units (ESUs). Preferably, when filtering is performed, the low-pass filter is set to allow EEG signals with a frequency of 32 Hz and less to pass. More preferably, the filter allows EEG signals with a frequency of 30 Hz and less to pass. More preferably still, the low-pass filter allows EEG signals with a frequency of 24 Hz and less to pass. Even more preferably, the low-pass filter allows EEG signals with a frequency of 16 Hz and less to pass.

Another step in various embodiments involves analyzing an epoch of predetermined size of the first derivative of the EEG signal using at least one suppression detection parameter, the at least one suppression detection parameter being used to detect suppression in the EEG signal. The suppression detection measure can be virtually any type of operator or algorithm which is capable of detecting the drastic changes in the EEG signal which may be representative of burst and suppression periods. Such suppression detection measures may include, but are not limited to the median absolute value, the peak-to-peak time measurement, root mean square (RMS), spectral measures, entropy measures, energy operators, and the like. Preferably, at least one suppression detection measure used is the median absolute value of the first derivative of the EEG signal. The median absolute value is a robust measure of the rate of change of EEG, is less sensitive to outliers, and corresponds with the visual recognition rules of suppression detection. Thus, as the EEG, or other physiological signal, is acquired, the processor first calculates the first derivative of that signal, and essentially simultaneously computes at least the median absolute value of that first derivative signal.

Still another step in various embodiments of the present invention involves utilizing the above calculated suppression detection measure (i.e., median absolute value) for the detection of suppression periods in the EEG signal. If the above calculated suppression detection measure (i.e., median absolute value) is below a predetermined threshold for a predetermined amount of time, then that particular epoch is determined to be suppression.

Some embodiments include a step in which the suppression periods are confirmed by the existence of burst periods in the last minute to ensure that low-amplitude EEG activity is not detected as suppression, while still making sure that slight EEG activity during suppression periods between the bursts doesn't preclude the detection of suppression. If the above calculated suppression detection measure (i.e., median absolute value) is above another predetermined threshold for a predetermined amount of time, then that particular epoch is determined to be burst. Preferably, the suppression periods are confirmed based on at least 10 seconds of burst in the last minute. More preferably, the suppression periods are confirmed based on at least 5 seconds of burst in the last minute. More preferably still, the suppression periods are confirmed based on at least 3 seconds of burst in the last minute. Even more preferably, the suppression periods are confirmed based on at least 1 second of burst in the last minute. More preferably yet, the suppression periods are confirmed based on at least 0.5 seconds of burst in the last minute. Even more preferably still, the suppression periods are confirmed based on at least 0.25 seconds of burst in the last minute.

Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal.

Some embodiments of the present invention further include a step by which the thresholds used for detecting a burst or suppression period are automatically relaxed or tightened based on environmental factors. For example, if the signal contains a particularly strong or high amplitude period of burst activity, the threshold may be relaxed so the results of the detection methods are not artificially skewed or misidentified.

Still further embodiments of the present invention may involve using the second-derivative of the EEG signal to perform the suppression detection methods. In such embodiments, similar methods may applied wherein suppression detection measures such as the median absolute value, mean, median, RMS, peak to peak, spectral measures, entropy measures, energy operators, or the like are used to calculate their respective values, and those values compared against appropriate thresholds to determine whether suppression or detection is occurring.

Still another step in various embodiments of the present invention involves outputting a signal based at least in part on the occurrence of suppression in the EEG signal to a device for communicating the outputted signal to a clinician monitoring the patient. This output signal may be any form of signal designed to get the clinician's attention and alert her to the fact that suppression has recently or is presently occurred. Preferably, the output signal is the percentage of suppression detected in the EEG signal during the last minute, known as suppression ratio (SR). It may also include audio warnings or alarms, or visual indicators on a monitor such as a text warning, flashing windows, colors, and the like, or any combination thereof.

Other embodiments may include the step of outputting a signal based at least in part on the occurrence of suppression in the EEG signal to a device for controlling the patient's level of anesthesia and amount of suppression. In this step, rather than alerting a clinician to the occurrence of suppression in a subject under anesthesia, the subject is instead attached to a closed-loop, or semi-closed-loop drug delivery device which automatically controls the amount of sedative or anesthetic being administered to the subject. The steps of the present invention and method can further include providing a drug or treatment to the subject or patient to counteract anesthesia and revive the subject or patient's brain function.

Some embodiments include a step in which artifacts are detected and identified, and are not counted as periods of burst activity. These artifacts may be those that were not detected by the front-end filtering, or new additional artifacts that corrupt the signal after initial filtering. In this optional step, the present invention differentiates between such artifacts and burst activity. This means that the system does not count an aberrant artifact as burst activity and thus effect the detection of burst and suppression periods and their durations. This is another step to increase the accuracy of the invention in environments that create artifacts in the EEG signal.

Some embodiments of the present invention further include a step by which the thresholds used for determining whether activity is burst or suppression are automatically relaxed or tightened based on environmental factors. For example, if the signal contains a particularly strong or high amplitude period of burst activity, the threshold may be relaxed so the results of the detection methods are not artificially skewed or misidentified.

Still further embodiments of the present invention may involve using the second-derivative of the EEG signal to perform the suppression detection methods. In such embodiments, similar methods may applied wherein suppression detection measures such as the median absolute value, mean, median, RMS, peak to peak, spectral measures, entropy measures, energy operators, or the like are used to calculate their respective values, and those values compared against appropriate thresholds to determine whether suppression or detection is occurring.

Now referring to the FIGS. 1-4, FIGS. 1A and 1B are block diagrams of two possible embodiments of a system for monitoring and real-time therapy applications. The system shown in FIGS. 1-4 can be adapted with modifications for other types of sensor signals described within this application. The system can be connected to the subject either on the subject's scalp 5 with mounted surface electrodes 1, intra-cranial cortical grids 4, or implanted deep brain electrode(s) 3. The electrode leads 6 are preferably connected to the system via a yoke 2 containing cardiac defibrillation resistors (not shown) designed to absorb the energy of a cardiac defibrillation pulse. These resistors (not shown) and the associated electronics in the front-end of the instrumentation amplifiers (not shown) are designed to protect the instrumentation electronics and in particular applications to have electromagnetic interference filters (EMF) to eliminate interference caused by other electrical devices, while still ensuring that most of the energy delivered by the pulse is used for the intended therapy.

The brainwave signals are then amplified and digitized by an analog-digital converter (ADC) circuitry 7. In addition, a signal quality (SQ) circuitry 8, 9 can be used to inject measurement currents into the leads 6 in order to calibrate the instrumentation amplifiers (not shown) and measure electrode impedance. Similar SQ circuitry 8, 9 monitors the front-end amplifiers in order to detect eventual saturation that occurs when leads 6 are disconnected. This information, along with the digitized brainwave signals, is relayed to the processor 10, 11, 12, 13, 14.

The processor is composed of the sub-systems 10, 11, 12, 13 14. The signal quality assessment module 10 is used to check whether each signal acquired by the system is of sufficient quality to be used in the subsequent analysis. This is done by continuously measuring the electrode impedance of each brainwave channel, and by quantifying the levels of 50 and 60 Hz noise in the signal. High levels of 50 or 60 Hz indicate either a poor electro-magnetic environment, or a poor connection to the patient which will result in a heightened sensitivity of the system for any other environmental noise (e.g., lead movement, vibration, etc.). High levels of 50 or 60 Hz noise are usually indicative of poor signal quality.

If the signal quality is good, the signal enters into the suppression detection module 11 of the system. First, the first derivative of the EEG signal is computed. This first derivative is now the signal that will be used for further burst and suppression analysis, not the raw (or filtered) EEG signal. The system utilizes at least one suppression detection parameter that will be used to determine if suppression is occurring in the EEG signal. The suppression measures computation module 11*a* is where the processor calculates the values of the various (at least one) suppression detection parameters based on the first derivative of the acquired EEG signal. Then, once the values for those measures have been calculated, those values are compared against a predetermined threshold value in the suppression detection decision module 11*b*. Here, if the suppression detection measure value falls above or below (depending on the particular measure in question) the predetermined threshold value for a predetermined amount of time, then the system determines that suppression is present in the EEG signal.

Next, in some embodiments, the system proceeds by analyzing the acquired signals in order to detect the presence of environmental or physiological artifacts (not shown), which may be corrupting the signal. This analysis is performed in the artifact detection and removal module 12. Preferably, artifact detection methods and systems such as those described in U.S. Patent Publication No. 2011-0295142 are used for the artifact detection and removal process, and that publication is herein incorporated by reference. Preferably, several artifact detection methods or algorithms are used in combination. These artifact detection methods or algorithms analyze the signal for artifacts using combinations of both sensitivity and specificity methods or algorithms, each detecting the presence of artifacts in different ways, and those measures are combined to increase the accuracy of artifact detection in the combination and decision module (not shown, subset of artifact detection and removal module 12.

De-noised and artifact-free signals are sent to the brainwave analysis/processing module 13. This sub-system derives information contained in the signal, such as the level of consciousness of the patient, the presence of electro-cortical silence, the level of ocular activity (EOG), the level of muscle activity (EMG), etc. This information can be used as a complement to the signal acquisition to provide a better diagnostic means to the user. Some of this information may also be used in the signal acquisition and suppression detection to tune properly the different thresholds used by the underlying algorithm.

A user interface module 14 provides the means for the user to interact with the system. In a preferred embodiment, this is done through the use of a display module 15, which can be a touch screen display, or any other variety of display device. The display module 15 is used to provide information (i.e., display the physiological signal, various indexes pertaining to the signal, suppression information, as well as provide the user a visual representation for inputting information when necessary). In addition, the user interface module 14 archives all the acquired signals and processed variables into a mass storage device 16, for later review.

The mass storage device 16 is used as a long term storage archive for all of the acquired EEG signals as well as the accompanying processing results. These data will then be available for later use. The signals will then be available for historical use and review where clinicians or researchers can check for burst and suppression, artifacts or other abnormal brain activity and the like. An artifact free EEG signal can be stored in the mass storage device 16 or a corrupted signal can be stored as well with the artifacts identified as part of the signal. Furthermore, they can be used as a database from which signals can be used for baseline determination or calibration of suppression or artifact detection techniques.

Finally, in some embodiments, the system is connected to a mechanism that automatically delivers a treatment to the patient, referred in the schematic as the treatment delivery device 18. The output of the system through a processor 10-14 can be used with the treatment delivery device including a processor 10-14 in closed loop 17, partially closed loop or open loop to automatically deliver physical, electrical or chemical treatment to the subject automatically based on the occurrence of abnormal brain activity, and monitor the effectiveness of such treatment in real time.

Figure 1B:
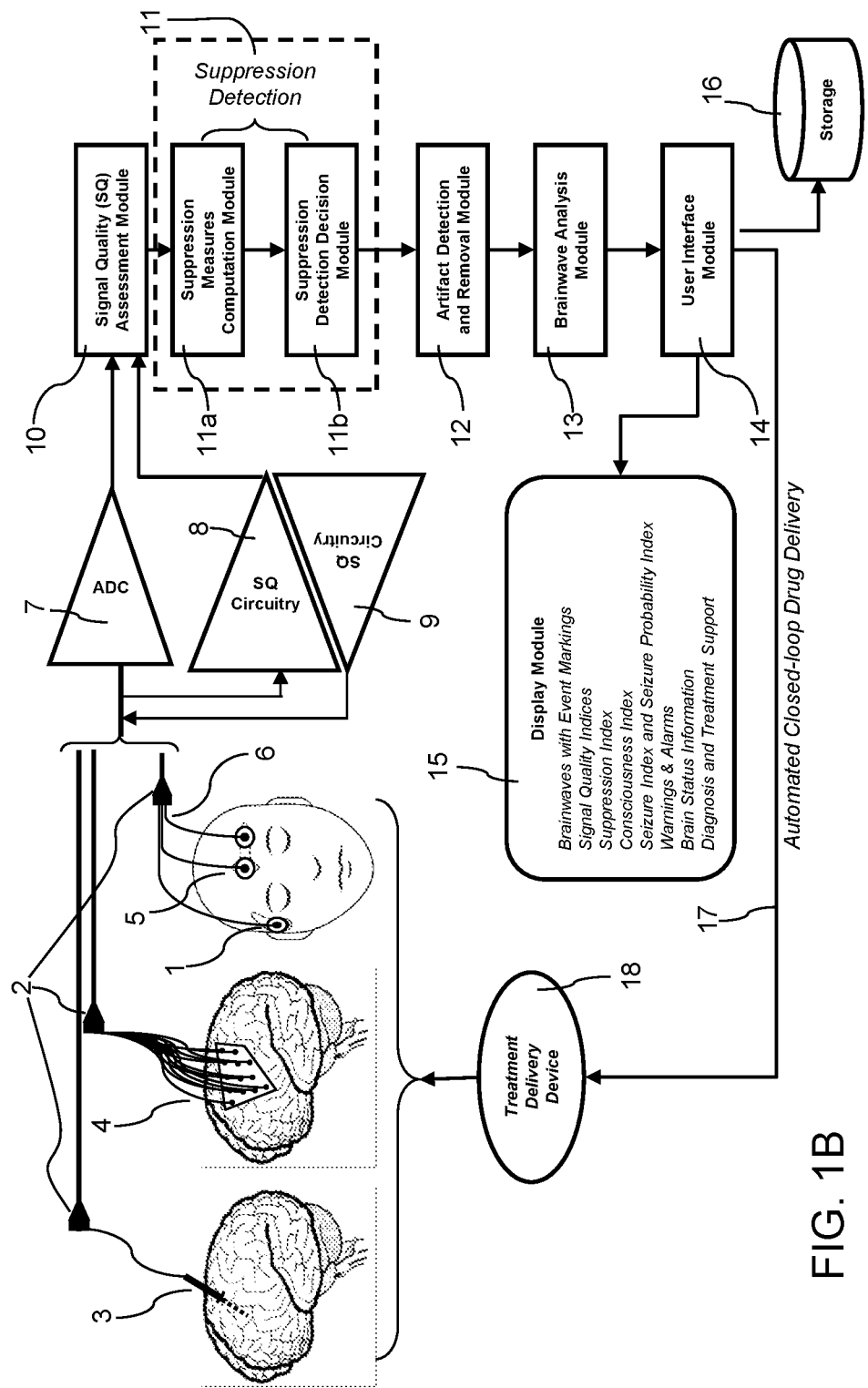
FIG. 1B. Block diagram of a system overview for real-time applications of the invention wherein a closed-loop treatment delivery device is used to administer medication or treatment when necessary based on level of consciousness and amount of suppression occurring.
Figure 2:
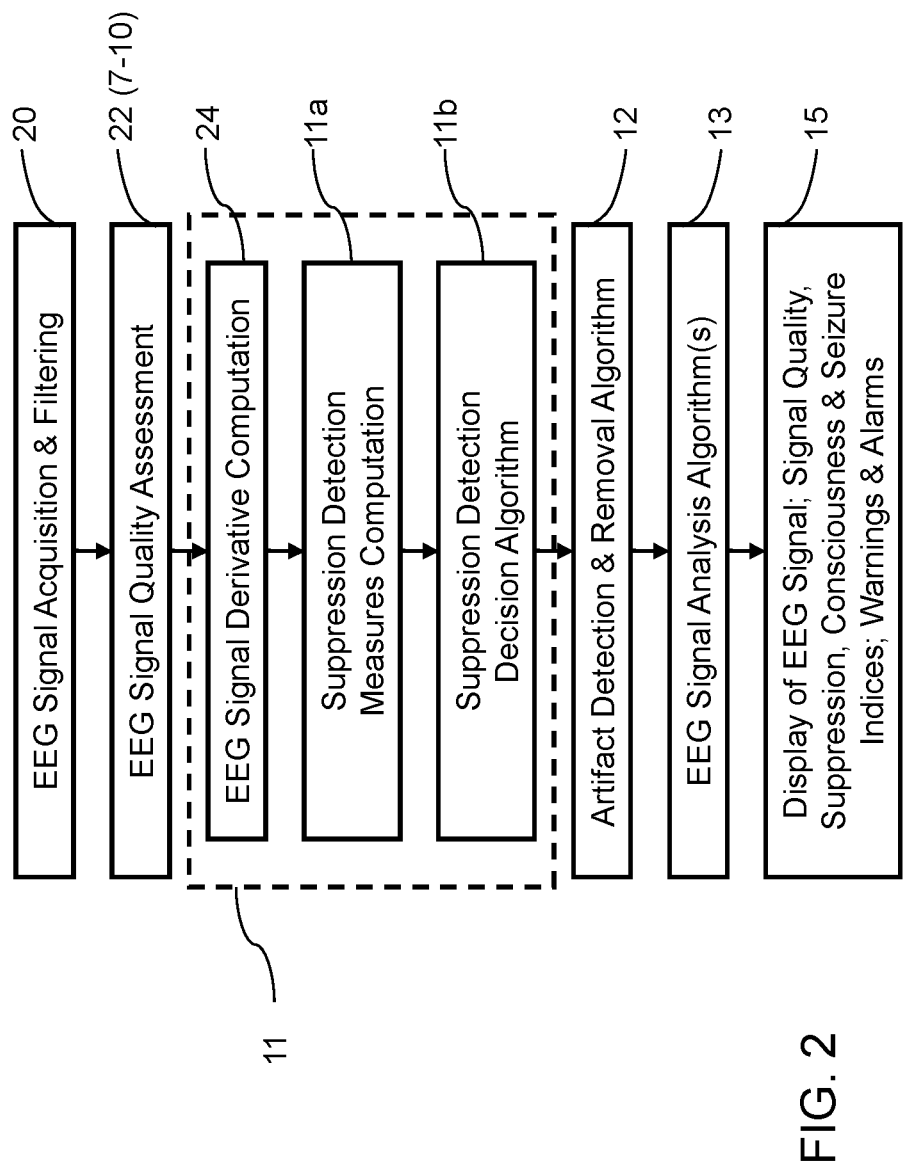
FIG. 2. Flowchart depicting one embodiment of the present invention wherein the first derivative of the EEG signal is analyzed to determine whether EEG suppression is occurring in a subject.

FIG. 2 is a flowchart of the overall signal acquisition and suppression detection process of the present invention. First, in the signal acquisition and filtering step 20, the EEG signal is acquired according to the method described above and may optionally have a front-end hardware filter applied to remove any HF interference or other electrical noise that may be present and corrupting the signal. Next, in the signal quality assessment step 22 (a combination of references 7-10 in FIGS. 1A and 1B), the incoming signal is checked for quality by means of impedance measurement of the electrodes. Other methods of signal quality measurement may be used alternatively, or in conjunction with the impedance measurement. Regardless of the methods of quality measurement used, only a signal with sufficient quality is useful for performing further analysis. Low quality signals are far more likely to produce inaccurate results or produce incorrect identifications of burst and suppression periods in the signal. If signal quality is sufficient, however, the system can proceed to the next step of suppression detection 11.

The suppression detection phase 11 is the core of the present invention. In all embodiments, the present invention first computes the first derivative 24 of the EEG (or other physiological) signal. Again, the first derivative represents the rate at which the amplitude of the raw (or filtered) EEG signal is changing and thus is useful for alerting the user or clinician when the amount of fluctuations in the EEG signal increase or decrease. A rapid decrease in brain activity (soma potential) may be indicative of suppression of the signal and thus the system may alert the clinician or user, in an open loop system, or appropriately adjust the level of medication, anesthetic, or sedative in a closed-loop system.

Then, various parameters of the first derivative of the acquired signal are measured and analyzed in the suppression detection measures computation step 11*a*. At least one suppression detection measure is used to analyze the first derivative of the signal for periods of suppression. In all embodiments, the preferred suppression detection measure is the median absolute value of an epoch of predetermined size of the first derivative of the signal. When the system computes the median absolute value of the first derivative of the signal, it is compared against a predetermined threshold value in the suppression detection decision algorithm 11*b*. The predetermined threshold is set at a value which has been determined through testing and training of the algorithm, to be above or at about the maximum value for the median absolute value of the first derivative of a suppressed EEG signal. Therefore, if the computed median absolute value is below that threshold value, the suppression detection algorithm determines that particular epoch to be a period of suppression.

Although at least one suppression detection measure (i.e., median absolute value) is all that is required, more preferably at least two suppression detection algorithms are used. More preferably still at least three suppression detection measures are used. Still more preferably still at least four suppression detection measures are used. Even more preferably at least five suppression detection measures are used. When more than one suppression detection measure is used to determine the presence of suppression periods in the signal, again, at least one is the median absolute value of the first derivative of the acquired signal. In such embodiments, the additional suppression detection measures may include, but are not limited to, peak-to-peak amplitude, root mean square (RMS), spectral measures, entropy measures, energy operators, and the like.

The artifact detection and removal algorithm 12 is an optional additional step involved in a complete physiological signal recording system. Artifact detection and removal may occur before or after suppression detection. Preferably, if artifact detection is used in the system, at least two artifact detection algorithms or measures are used for providing probabilities of the presence of true and false artifacts in the acquired signal: at least one for sensitivity and at least one for specificity. Sensitivity methods, processes or algorithms are those that are designed to be or happen to be more accurate and useful for the detection and/or calculation of the presence and/or probability of the presence of real artifacts in an EEG, other physiological signal or other sensor signal. Specificity methods, processes or algorithms are those that are designed or happen to be more accurate and useful for the detection and/or calculation of the absence and/or probability of the absence of artifacts, in an EEG, other physiological signal, or other sensor signal. Another way to describe these two types of methods, processes or algorithms is that those for sensitivity test for the percentage of accurate detections when presented with true artifacts whereas those for specificity test for the percentage of accurate non-detections when presented with a signal with no artifacts.

The signal analysis algorithms 13 are those that perform any further analysis on the signal and additional information is calculated or otherwise retrieved from the signal. Such algorithms may include, but are not limited to those for retrieving other physiological signal activity (i.e., ocular activity, muscle activity, and the like), level of consciousness, individual brain hemisphere activity, calculated indexes corresponding to these values, and any combination of these or other metrics or features that may be drawn from the acquired physiological signal.

The display module 15 again is used to show any combination of metrics, signals or features of the signal and analysis that may be relevant or desired. Such features may include the original physiological signal, a filtered signal, the first or higher derivatives of the acquired signal, event markers accompanying the various signals, signal quality indexes, the suppression index, consciousness index, seizure index and seizure probability index, warnings and alarms, brain status information, diagnosis and treatment support, and the like. Additionally, the display may include audio signals such as beeps, alarms, whistles or the like for the purpose of alerting the user or clinician of potential problems or issues.

Figure 3:
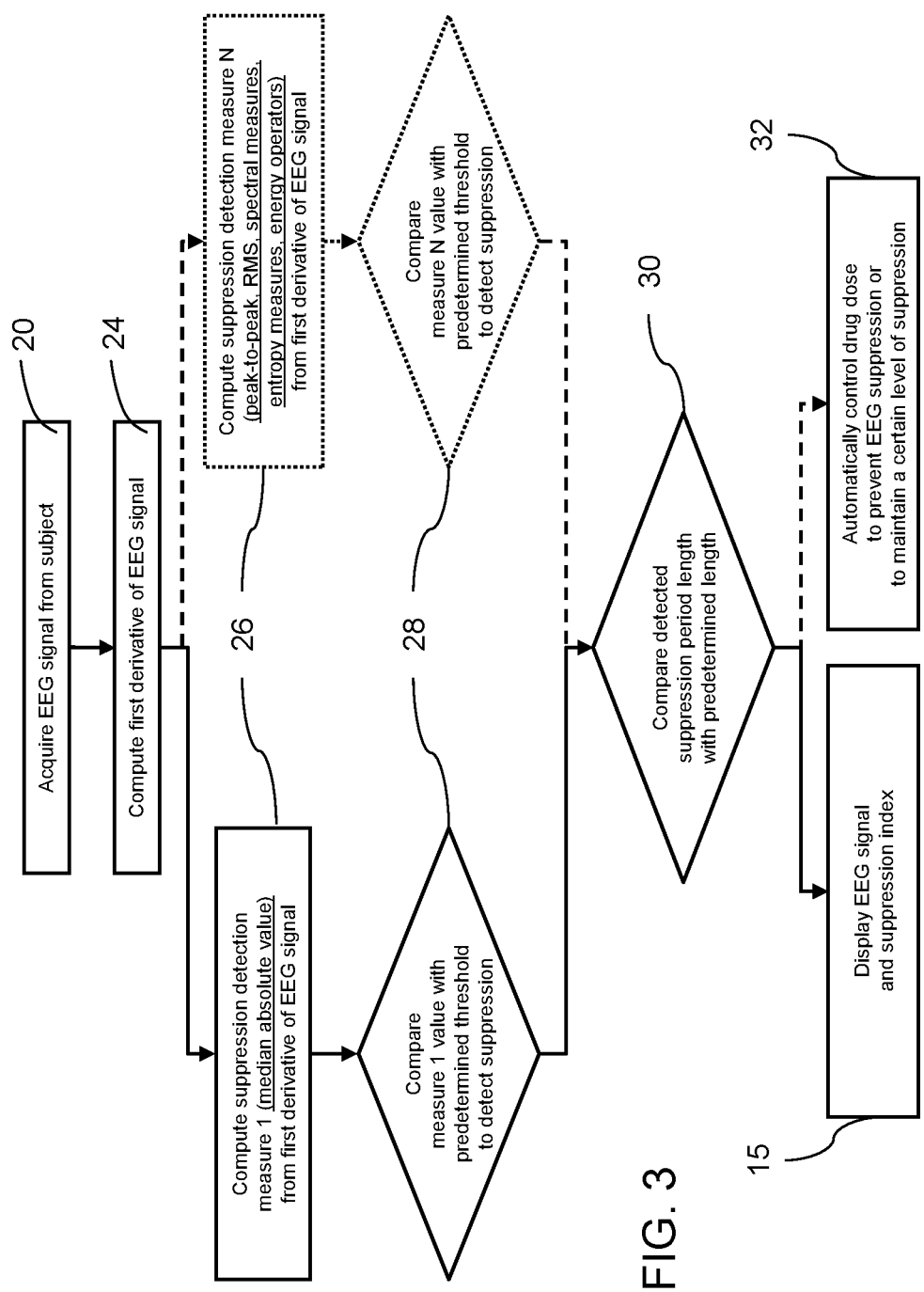
FIG. 3. Flowchart depicting one embodiment of the present invention wherein multiple suppression detection parameters are used to analyze the first derivative of the EEG signal in order to determine whether EEG suppression is occurring and information is displayed for user to interpret and provide appropriate treatment and possibly transmitted to closed-loop treatment delivery device to automatically administer appropriate medication or treatment.

FIG. 3 is a flow chart depicting the process for suppression detection as graphically depicted in FIGS. 1A and 1B, wherein the system provides at least signal and suppression information to a display device for user or clinician for evaluation and action, and/or a closed-loop treatment delivery device for automatic administration and adjustment of medication. The first step is to acquire the EEG signal 20 from the patient or subject as described above. The EEG (or other physiological signal) may optionally be filtered (not shown) upon acquisition. The raw or filtered signal is then transmitted or transferred to the processor (FIGS. 1A and 1B, references 10-14), which calculates the first derivative of the acquired signal 24. Once the first derivative is calculated, the suppression detection measures 26 or algorithms are applied to that derivative. Other embodiments (not shown) may apply the suppression detection measures or algorithms to a higher derivative of the signal. The suppression detection measures or algorithms, as listed before, include at least the median absolute value of the first derivative of the signal, and may also include other measures including, but not limited to, peak-to-peak amplitude, root mean square (RMS), spectral measures, entropy measures, energy operators, and the like.

Each of the suppression detection measures used produces a value for that measure corresponding to the appropriate calculation. Those values are then compared against predetermined threshold values 28, each measure having its own independent value calculation and corresponding threshold value. For each suppression detection measure, its calculated value is compared to the predetermined threshold value and a determination of whether suppression is or was occurring in the acquired signal is provided based on whether the calculated suppression detection measure value is above or below the predetermined threshold.

The signal is broken up into discreet sampling windows for purposes of performing the analysis. The signal sampling window is preferably about 3 seconds long, more preferably about 2 seconds long, even more preferably about 1 seconds, and most preferably about 0.5 seconds long. Depending on the embodiment, the various suppression detection measures are calculated 26 for each such sampling window and compared against the appropriate threshold 28 for each particular measure used. If the suppression detection value is below the threshold for that particular measure, then that sampling window is determined to exhibit suppression and is flagged. This process is then repeated for each subsequent consecutive signal sampling window, resulting in each window being either flagged as exhibiting suppression or cleared as not showing suppression of the EEG signal. The more consecutive sampling windows in which there is suppression detected by the above method, the more likely it is that actual and potentially harmful suppression is occurring in the signal.

In some embodiments of the present invention, the detection of suppression periods of the signal is accompanied by detection of burst periods. In such embodiments, the detection measures obtained from the first derivative of the acquired physiological (EEG) signal are analyzed for both the burst and suppression detection. Quite often, suppression, which is the condition being targeted by the present invention, is shortly or immediately preceded by a burst of cortical activity or soma potential. Therefore, some embodiments utilize a burst detection algorithm to help increase the accuracy of the suppression detection algorithm. Based on the independent detection of burst and suppression in the first derivative of the signal, the likelihood that the system accurately and properly identifies periods of suppression greatly increases. In such embodiments, the burst must precede the suppression period. Preferably, for the detected burst period to more accurately indicate an oncoming suppression period, the burst period should be longer than 0.5 seconds and at least 1 burst should occur within 1 minute preceding a detected suppression period. More preferably, the burst period should be longer than 0.5 seconds and at least 2 bursts should occur within 1 minute preceding a detected suppression period. Even more preferably, the burst period should be longer than 0.5 seconds and at least 3 bursts should occur within 1 minute preceding a detected suppression period. More preferably, still the burst period should be longer than 0.5 seconds and at least 4 bursts should occur within 1 minute preceding a detected suppression period. Even still more preferably, the burst period should be longer than 0.5 seconds and at least 5 bursts should occur within 1 minute preceding a detected suppression period. Most preferably, the burst period should be longer than 0.5 seconds and at least 6 bursts should occur within 1 minute preceding a detected suppression period.

Once the suppression detection measures have been calculated and compared against the threshold value, and the resulting determination of whether suppression occurred is made for each sampling window, the next step is to determine whether the suppression (assuming it was determined to have occurred) is of a long enough duration to constitute clinically relevant suppression of the EEG signal. In other words, each individual sampling window may exhibit suppression, but those windows are each small enough that it requires several suppressed samples in consecutive succession to warrant a clinical concern for the patient. As noted above, suppression is typically longer than periods of burst activity, and usually lasts for at least about 5 seconds. Therefore, when one sampling window exhibits suppression, a count is started to determine how long the detected suppression lasts. That length of suppression time is compared against a predetermined value 30 which is used to decide whether actual EEG suppression that is clinically relevant has occurred.

This entire process is preferably performed in real-time as the signal is acquired from the patient. Therefore, as the signal is acquired, the above analysis is performed and the determination of whether suppression has occurred is continuously updated. As these steps are continuously performed, the EEG signal and a suppression index are displayed 15 for a clinician or other user to monitor. These values may be output on a screen or monitor attached to the monitoring equipment or in close proximity thereto, or may be sent to a remote location or handheld device such as a phone, palm pilot, tablet or other computer. Once the appropriate information, particularly the suppression index communicating to the clinician or other user the level, amount or severity of any occurring suppression is output or otherwise displayed, the clinician or other user is then able to act accordingly and take the necessary steps to ensure the patient's safety and recovery, and minimize potential harm to the patient.

Additionally, and optionally, the system may include a closed-loop treatment delivery device 17, 18. Therefore, another optional step is to utilize the suppression detection output to automatically administer treatment or deliver a drug or medication 32 to the patient. In such a step, the suppression index would be used by an automated protocol to determine the appropriate steps necessary to cause the patient to recover from the prolonged suppression and to carry out that treatment, much as the clinician or user would, but automatically.

Figure 4:
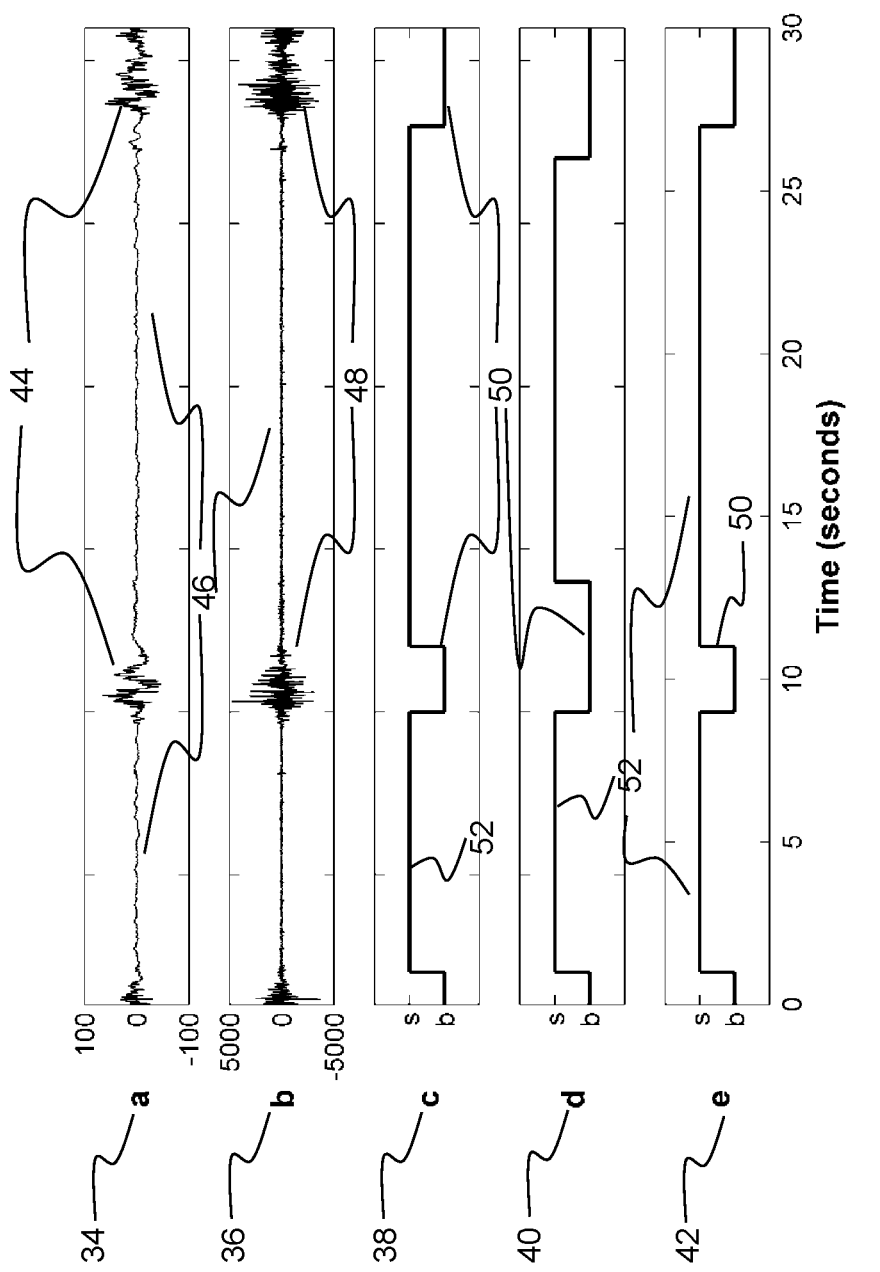
FIG. 4. Series of graphs showing the original EEG signal, the first derivative EEG signal, and the results of three suppression detection methods.

FIG. 4 depicts a series of acquired biopotential signals, specifically EEG signals along with the results of three different suppression detection methods. These graphs represent the signal at various phases in the process and how each method of detecting suppression in the signal performs relative to the others.

Graph 'a' 34 depicts a sample EEG segment as recorded with only the basic filtering methods described above. No analysis has been performed on the EEG signal, nor any transformation, other than removal of front-end noise and artifacts. The graph depicts the level of brain activity (vertical axis) over time (horizontal axis). Periods of suppression 46 are characterized by very low amplitude brain activity, and are typically interrupted by brief periods of burst activity 44 which are characterized by high amplitude, but short-duration brain activity.

Graph 'b' 36 depicts the calculated first derivative of the EEG signal segment shown in graph 'a' 34. As those skilled in the art understand, the first derivative represents the rate at which the signal is changing, in this case, amplitude. Thus, this graph represents the rate of change of the brain activity (vertical axis) as time (horizontal axis) passes. The periods of suppression 46 in the first derivative signal 36 appear largely similar in duration to those shown in the raw EEG signal 34 because during a given period of suppression 46 the signal is not changing amplitude significantly. Conversely, during periods of burst activity 44, the EEG signal 34 changes quite rapidly and thus the first derivative 36 will reflect larger amplitudes of change 48 for the duration of that burst activity 44. This first derivative signal 36 is the signal on which the present invention performs the analysis and calculation.

Graphs 'c' 38, 'd' 40, and 'e' 42 each represent the results of a different suppression detection method. The vertical axis of each graph is labeled by an 's' and a 'b' representing the detection of suppression periods 52 and periods of burst activity 50 as determined by the given detection method. Again, the horizontal axis represents time.

Graph 'c' 38 represents the traditional method of visual detection. As described above, this method requires a trained individual to either view a printout of the EEG signal 34 or view the EEG signal 34 on a monitor (not shown) in real time. The signal 34 would be then visually inspected for periods of time, typically longer than 0.5 s, where the peak-to-peak amplitude of the EEG signal is much less (typically 5 to 20 µV) and flagged as representing suppression 52 of the signal. When compared against the actual EEG signal in graph 'a' 34, it is clear that this traditional visual method of identifying suppression 52 (and burst 50) periods may be quite accurate. The trained user can be very efficacious in identifying the points where burst 50 and suppression 52 occur in the actual EEG signal 34. However, as noted above, this accuracy cannot be guaranteed because each individual user may have a subjective opinion of those distinct periods of activity, particularly when the signal is not as precise and clean as the one depicted in graph 'a' 34. Additionally, this visual method is very time intensive, requiring the trained user typically to look at a printout of the signal significantly later than the signal is being recorded, as well as expensive.

Graph 'd' 40 represents the results of other automated suppression detection methods. Existing automated methods perform the analysis and detection on the original EEG signal as shown in graph 'a' 34, much like the traditional, visual method. The results of such other automated methods clearly show a less accurate detection of suppression periods 52 as well as burst periods 50. The suppression period 52 appears to be of a much longer duration than either the raw signal 34 shows or as identified by a trained user detecting visually in graph 'c'. This is likely due to the sensitive nature of the algorithms required to perform the identification in automated systems. When a period of burst activity 44 in the original EEG signal 34 ends, it does not do so abruptly. Like all wave activity, it dampens out rather than simply dropping from high amplitude activity down to a comparably flat signal. This can be seen by looking at the transition from burst activity 44 to suppression period 46 in graph 'a' 34. The signal gradually dampens from the high amplitude burst 44 to the very low amplitude suppression 46. As a result, where the trained user is able to discern the apparently subtle difference between the burst 44 and suppression 46 in that nebulous dampening area, other automated algorithms cannot obtain the same level of accuracy. As a result, existing automated detection methods provide artificially inflated periods of burst activity 50, and typically artificially shortened periods of suppression 52 in the signal. Clearly, such methods are not nearly as accurate as the traditional method, and although they are much quicker and cheaper to use, the loss of accuracy can prove harmful to the patient if it leads to misapplication of anesthetics, sedatives or other drugs.

Graph 'e' 42 represents the results of the present invention's suppression detection methods. These methods utilize the first derivative 36 of the original EEG signal 34, rather than that original signal 34 itself. The results of the present automated method 42 are equivalent in accuracy to the traditional visual method 38. Furthermore, the present automated detection method 42 is not susceptible to the subjective nature of human review that is prevalent and inherent to the traditional visual method 38. The burst periods 50 and suppression periods 52 as detected by the present automated method 42 are virtually identical to those detected by the trained user using the traditional visual method 38. Clearly, both the traditional visual method 38 and the present automated method 42 are more accurate than other existing automated methods. Therefore, it is shown in graph 'e' 42 that the present automated method is at least as accurate as the most accurate existing detection method; however, this method further provides the added benefits of providing that accuracy at a reduced cost (no need to pay a trained clinician to sit down and read the EEG signal), and also is much quicker than the traditional visual method 38, and can even be used in real-time applications. The present method combines all of the benefits of the other two methods (visual and existing automated methods) while eliminating the major drawbacks of each as well.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claims:

1. A system for monitoring a subject or patient under anesthesia comprising:
    at least two electroencephalography (EEG) electrodes adapted for acquiring an EEG signal from the subject or patient, wherein the EEG signal is a substantially continuous time domain signal;
    an analog-digital converter adapted for amplifying and digitizing the EEG signal
    a processor configured to apply an algorithm to compute a first derivative of the EEG signal directly from the EEG signal, configured to determine from the first derivative of the EEG signal at least one suppression detection parameter from a group consisting of: mean absolute value, mean, median, median amplitude, root mean square (RMS), peak to peak, standard deviation, spectral measures, entropy measures, and energy operators, wherein the processor is further configured to compare the at least one suppression detection parameter against a respective predetermined threshold, and wherein the processor is further configured to determine whether a level of suppression has occurred when the at least one detection parameter meets or exceeds the respective predetermined threshold for a predetermined time duration;
    an output module adapted to output the level of suppression detected by the processor with the algorithm for the patient or subject under anesthesia; and
    an anesthesia treatment delivery device for the subject or patient, wherein a medication of the anesthesia treatment delivery device is adjusted based, in part, on the level of suppression determination.

2. The system of claim 1, wherein the at least one suppression detection parameter used by the algorithm of the processor is the median amplitude of the first derivative of the EEG signal.

3. The system of claim 1, wherein the processor is further configured to apply at least two artifact detection filters and/or algorithms prior to computing the first derivative of the EEG signal, at least one artifact detection and removal filter and/or algorithm for specificity and at least one artifact detection and removal filter and/or algorithm for sensitivity.

4. The system of claim 1, wherein the processor is configured to apply at least two suppression detection parameters, wherein one suppression detection parameter is the median amplitude of the first derivative of the EEG signal, and at least one suppression detection parameter is one of RMS, standard deviation, mean, spectral measures, entropy measures, and energy operators.

5. The system of claim 1, wherein the output module is configured to provide a warning to a clinician indicating that suppression is occurring in the subject or patient.

6. The system of claim 1, wherein the anesthesia treatment delivery device is configured to provide a drug or treatment to the subject or patient, wherein the drug or treatment is adapted to counteract anesthesia and revive the subject's or patient's brain function.

7. The system of claim 1, wherein the processor is further configured to detect burst activity utilizing a burst detection algorithm, the detected burst activity being indicative of an oncoming suppression activity when burst activity lasts longer than 0.5 seconds and at least one burst occurs within 1 minute preceding a detected suppression period.

8. A system for monitoring a subject or patient under anesthesia comprising:
    at least two electroencephalography (EEG) electrodes adapted for acquiring an EEG signal from the subject or patient, wherein the EEG signal is a substantially continuous time domain signal;
    an analog-digital converter adapted for amplifying and digitizing the EEG signal;
    a processor configured to apply a first algorithm and a second algorithm, the first algorithm is adapted to measure burst activity, and the second algorithm is adapted for computing a first derivative of the EEG signal directly from the EEG signal, and configured to determine, from the first derivative of the EEG signal, at least one suppression detection parameter from a group consisting of: mean absolute value, mean, median, median amplitude, root mean square (RMS), peak to peak, standard deviation, spectral measures, entropy measures, and energy operators, wherein the processor is further configured to compare the at least one suppression detection parameter against a respective predetermined threshold, and wherein the processor is further configured to determine whether a level of suppression has occurred when the at least one suppression detection parameter meets or exceeds the respective predetermined threshold for a predetermined time duration;
    an output module adapted to output the level of suppression detected by the processor with the second algorithm for the patient or subject under anesthesia; and
    an anesthesia treatment delivery device for the subject or patient, wherein a medication of the anesthesia treatment delivery device is adjusted based, in part, on the level of suppression output;
    wherein the measured burst activity by the first algorithm of the processor is used by the second algorithm as being indicative of an oncoming suppression activity when burst activity lasts longer than 0.5 seconds and at least one burst occurs within 1 minute preceding a detected suppression period for determining the level of suppression.

9. The system of claim 8, wherein the at least one suppression detection parameter used by the second algorithm of the processor is the median amplitude of the first derivative of the EEG signal.

10. The system of claim 8, wherein the processor is further configured to apply at least two artifact detection filters and/or algorithms prior to computing the first derivative of the EEG signal, at least one artifact detection and removal filter and/or algorithm for specificity, and at least one artifact detection and removal filter and/or algorithm for sensitivity.

11. The system of claim 8, wherein the processor is configured to apply at least two suppression detection parameters, wherein one suppression detection parameter is the median amplitude of the first derivative of the EEG signal, and at least one suppression detection parameter is one of RMS, standard deviation, mean, spectral measures, entropy measures, and energy operators.

12. The system of claim 8, wherein the output module is configured to provide a warning to a clinician indicating that suppression is occurring in the subject or patient.

13. The system of claim 8, wherein the anesthesia treatment delivery device is configured to provide a drug or treatment to the subject or patient or the system further includes a second device configured to provide the drug or treatment, wherein the drug or treatment is adapted to counteract the anesthesia treatment and revive the subject's or patient's brain function.

14. A system for monitoring a subject or patient under anesthesia comprising:
at least two electroencephalography (EEG) electrodes adapted for acquiring an EEG signal from a subject or patient, wherein the EEG signal is a substantially continuous time domain signal;
an analog-digital converter adapted for amplifying and digitizing the EEG signal;
a processor with an algorithm configured to compute a first derivative of the EEG signal directly from the EEG signal, configured to determine from the first derivative of the EEG signal at least one suppression detection parameter from a group consisting of: mean absolute value, mean, median, median amplitude, root mean square (RMS), peak to peak, standard deviation, spectral measures, entropy measures, and energy operators, wherein the processor is further configured to compare the at least one suppression detection parameter against a respective a predetermined threshold, and wherein the processor is further configured to determine whether a level of suppression has occurred when the at least one suppression detection parameter meets or exceeds the respective predetermined threshold for a predetermined time duration;
an output module adapted to output the level of suppression detected by the processor with the algorithm for the patient or subject under anesthesia; and
an anesthesia treatment delivery device for the subject or patient, wherein a medication of the anesthesia treatment delivery device is adjusted based, in part, on the level of suppression determination;
wherein the anesthesia treatment delivery device is configured to provide a drug or treatment to the subject or patient or the system further includes a second device configured to provide the drug or treatment, wherein the drug or treatment is adapted to counteract the anesthesia treatment and revive the subject's or patient's brain function.

15. The system of claim 14, wherein the at least one suppression detection parameter used by the algorithm of the processor is the median amplitude of the first derivative of the EEG signal.

16. The system of claim 14, wherein the processor is further configured to apply at least two artifact detection filters and/or algorithms prior to computing the first derivative of the EEG signal, at least one artifact detection and removal filter and/or algorithm for specificity and at least one artifact detection and removal filter and/or algorithm for sensitivity.

17. The system of claim 14, wherein the processor is configured to apply at least two suppression detection parameters, wherein one suppression detection parameter is the median amplitude of the first derivative of the EEG signal, and at least one suppression detection parameter is one of RMS, standard deviation, mean, spectral measures, entropy measures, and energy operators.

18. The system of claim 14, wherein the output module is configured to provide a warning to a clinician indicating that suppression is occurring in the subject or patient.

19. The system of claim 14, wherein the processor is further configured to detect burst activity utilizing a burst detection algorithm, the detected burst activity being indicative of an oncoming suppression activity when burst activity lasts longer than 0.5 seconds and at least one burst occurs within 1 minute preceding a detected suppression period.

20. The system of claim 14, wherein the processor is further configured to measure level of consciousness of the patient or subject.

\* \* \* \* \*